(12) United States Patent
Pyun et al.

(10) Patent No.: US 9,840,506 B2
(45) Date of Patent: Dec. 12, 2017

(54) CRYSTAL OF DORIPENEM, AND PREPARATION METHOD THEREFOR

(71) Applicant: JW PHARMACEUTICAL CORPORATION, Seoul (KR)

(72) Inventors: Do-Kyu Pyun, Gyeonggi-do (KR); Kyoung-Jin O, Gyeonggi-do (KR); Sang-A Lee, Seoul (KR); Ji-Hyun Jung, Gyeonggi-do (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 0 days.

(21) Appl. No.: 15/307,203

(22) PCT Filed: Apr. 15, 2015

(86) PCT No.: PCT/KR2015/003760
§ 371 (c)(1),
(2) Date: Oct. 27, 2016

(87) PCT Pub. No.: WO2015/167148
PCT Pub. Date: Nov. 5, 2015

(65) Prior Publication Data
US 2017/0050969 A1    Feb. 23, 2017

(30) Foreign Application Priority Data

Apr. 28, 2014  (KR) .................. 10-2014-0050698

(51) Int. Cl.
*C07D 477/20*   (2006.01)
*C07D 477/10*   (2006.01)
*C07D 477/12*   (2006.01)

(52) U.S. Cl.
CPC ......... *C07D 477/20* (2013.01); *C07D 477/10* (2013.01); *C07D 477/12* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,111,098 A | 8/2000 | Inoue et al. |
| 7,767,809 B2 | 8/2010 | Uenaka |
| 8,247,402 B2 | 8/2012 | Saitoh et al. |
| 8,822,445 B2 | 9/2014 | Huang et al. |
| 2003/0153191 A1 | 8/2003 | Saitoh et al. |
| 2006/0229285 A1 | 10/2006 | Uenaka |
| 2007/0060562 A1 | 3/2007 | Saitoh et al. |
| 2008/0207586 A1 | 8/2008 | Saitoh et al. |
| 2013/0059831 A1 | 3/2013 | Saitoh et al. |
| 2013/0079322 A1 | 3/2013 | Huang et al. |
| 2013/0090325 A1 | 4/2013 | Huang et al. |
| 2015/0031664 A1 | 1/2015 | Saitoh et al. |

FOREIGN PATENT DOCUMENTS

| | | |
|---|---|---|
| CN | 1896057 A | 1/2007 |
| CN | 101100468 A | 1/2008 |
| CN | 101100469 A | 1/2008 |
| CN | 101119997 A | 2/2008 |
| CN | 101348485 A | 1/2009 |
| CN | 101531623 A | 9/2009 |
| CN | 101880282 A | 11/2010 |
| CN | 102285988 A | 12/2011 |
| CN | 102977101 A | 3/2013 |
| CN | 103664947 A | 3/2014 |
| KR | 10-0314558 B1 | 2/2002 |
| KR | 10-0472842 B1 | 3/2005 |
| WO | 95/29913 A1 | 11/1995 |
| WO | 01/72750 A1 | 4/2001 |
| WO | 2004/072073 A1 | 8/2004 |
| WO | 2008/006298 A1 | 1/2008 |

OTHER PUBLICATIONS

A. Teruzo, et al., Solvent Handbook, pp. 47-51 (1976) (with English abstract).
H. Reimei, Preparing Organic Compound Crystal Handbook, pp. 10, 11, 57-81 (2008) (with English abstract).
Japanese Chemical Society, Experimental Chemistry Lecture 1, Basic Control, pp. 184-189 (1990) (with English abstract).
Japanese Chemical Society, Experimental Chemistry Guide Book (1992) (with English abstract).
Y. Iso, "Synthesis and Modification of a Novel 1 beta-Methyl Carbapenem Antibiotic, S-4661," The Journal of Antibiotics, vol. 49, No. 5, pp. 478-484 (1996).
S. Ling, "Process Improvement on the Synthesis of Doripenem," Guangzhou Chemical Industry, vol. 41, No. 21 (2013) with English abstract.

*Primary Examiner* — Deepak R Rao
*Assistant Examiner* — Laura M Daniel
(74) *Attorney, Agent, or Firm* — Fitzpatrick, Cella, Harper & Scinto (57) ABSTRACT

This invention relates to a novel doripenem crystal, a solvate thereof, and a preparation method thereof and, more specifically, to a novel doripenem anhydride crystal, a method of preparing the doripenem anhydride crystal using various solvents, and a solvate of doripenem.

14 Claims, 7 Drawing Sheets

CRYSTAL OF DORIPENEM, AND PREPARATION METHOD THEREFOR

CROSS REFERENCES TO RELATED APPLICATION

This application claims the benefit of Korean Patent Application No. KR 10-2014-0050698, filed Apr. 28, 2014 which is hereby incorporated by reference in their entireties into this application.

TECHNICAL FIELD

The present invention relates to a novel crystal of doripenem, a solvate thereof, and a preparation method thereof and, more particularly, to a novel doripenem crystal in anhydride form, a solvate of doripenem, and a method of preparing the doripenem crystal using various solvents.

BACKGROUND ART

The worldwide use of antibiotics for the treatment of infectious diseases has drastically increased over the last 40 years. Two million pounds of antibiotics were produced only in the United States in 1954, and the current production thereof amounts to over 50 million pounds, from which the extent of increase in the use of antibiotics may be estimated. Furthermore, in accordance with the Center for Disease Control and Prevention (CDC), 235 million doses of antibiotics are consumed by people yearly.

Doripenem is a carbapenem antibiotic that is active against a wide variety of gram-negative bacteria and gram-positive bacteria, and it has the chemical name of ((4R,6S)-6-((R)-1-hydroxyethyl)-4-methyl-7-oxo-3-(((3S,5S)-5-((sulfamoylamino)-methyl)pyrrolidin-3-yl)thio)-1-azabicyclo[3.2.0]hep-2-ene-2-carboxylic acid, and is represented by Chemical Formula 1 below.

[Chemical Formula 1]

Although doripenem is known for taking the form of Type 1 to V hydrate crystals, a Type IV doripenem hydrate crystal, currently commercially available, has low solubility and thus its suspension has to be diluted before use, which is undesirable.

In addition, a recrystallization process is performed to increase the quality of doripenem during the preparation thereof. As such, water is used as a solvent for dissolving doripenem. Taking into consideration the yield, a small amount of water is used, and adjusting the pH or increasing the temperature may be conducted to completely dissolve doripenem, but is problematic because the purity of doripenem may be decreased.

Meanwhile, Korean Patent No. 10-0472848 discloses a method of preparing Type III and Type IV doripenem hydrates, and Korean Patent No. 10-0314558 discloses Type I and Type II doripenem hydrates, in which the need to increase stability is described, but problems related to the increase in solubility of doripenem or the simplification of the preparation method thereof still occur.

Hence, it is required to provide doripenem that is simply prepared and has high solubility and stability.

DETAILED DESCRIPTION OF INVENTION

Technical Problem

To solve the above problems,
the present invention has been made keeping in mind the above problems encountered in the related art, and the present invention is intended to provide for the first time a novel doripenem anhydride, which is in the form of an anhydride crystal to increase solubility and stability, in lieu of a conventional doripenem hydrate.

In addition, the present invention is intended to provide for the first time a method of preparing a novel doripenem anhydride crystal, which enables the preparation of the novel doripenem anhydride crystal at room temperature within a short time.

In addition, the present invention is intended to provide a solvate of doripenem.

Technical Solution

To achieve the above goal,
the present invention provides a doripenem anhydride crystal.

In addition, the present invention provides a method of preparing a doripenem anhydride crystal, comprising: (1) dissolving doripenem in ethylene glycol or dimethyl sulfoxide; (2) adding a solution obtained in the step (1) to a mixture of methanol and water or a mixture of ethanol and water to produce a precipitate, the water being added in a volume of less than 15% but exceeding 0% based on a total volume of methanol or ethanol in the mixture; and (3) filtering and drying the precipitate in the step (2).

In addition, the present invention provides a method of preparing a doripenem anhydride crystal, comprising: (1) adding a Type III doripenem hydrate or a Type IV doripenem hydrate to any one selected from the group consisting of methanol, ethanol, a mixture of methanol and water, and a mixture of ethanol and water to produce a precipitate, the water being added in a volume of less than 15% but exceeding 0% based on a total volume of the mixture of methanol and water or the mixture of ethanol and water; and (2) filtering and drying the precipitate in the step (1).

In addition, the present invention provides a method of preparing a doripenem anhydride crystal, comprising: (1) adding amorphous doripenem to methanol or ethanol to produce a precipitate; and (2) filtering and drying the precipitate in the step (1).

In addition, the present invention provides a method of preparing a doripenem anhydride crystal, comprising: (1) dissolving doripenem in at least one selected from the group consisting of N-methyl-2-pyrrolidone (NMP), dimethylformamide (DMF) and dimethylacetamide (DMAC); (2) adding a solution obtained in the step (1) to a mixture of water and an organic solvent to produce a precipitate; and (3) filtering and drying the precipitate in the step (2).

In addition, the present invention provides a solvate of doripenem, characterized in that the solvent used therefor is ethylene glycol or dimethyl sulfoxide.

Advantageous Effects

According to the present invention, a method of preparing a novel doripenem anhydride crystal enables the preparation of the doripenem anhydride crystal at room temperature within a short time, without high-temperature filtration or drastic changes in pH.

In addition, the novel doripenem anhydride crystal, which is provided for the first time in the present invention, has high solubility. Thus, when doripenem is administered in vivo, the doripenem anhydride crystal of the present invention can be completely dissolved, and thus fixed-dose administration thereof is possible, unlike conventional methods in which a doripenem hydrate crystal is diluted and administrated in suspension form.

In addition, according to the present invention, the novel doripenem anhydride crystal can exhibit high stability.

MODE FOR INVENTION

Hereinafter, a detailed description will be given of the present invention.

The present invention addresses a Type VI doripenem anhydride crystal and a Type VII doripenem anhydride crystal. The present inventors have synthesized a novel doripenem anhydride crystal having remarkably increased solubility, compared to conventional crystal forms, thus culminating in the present invention.

Figure 2:
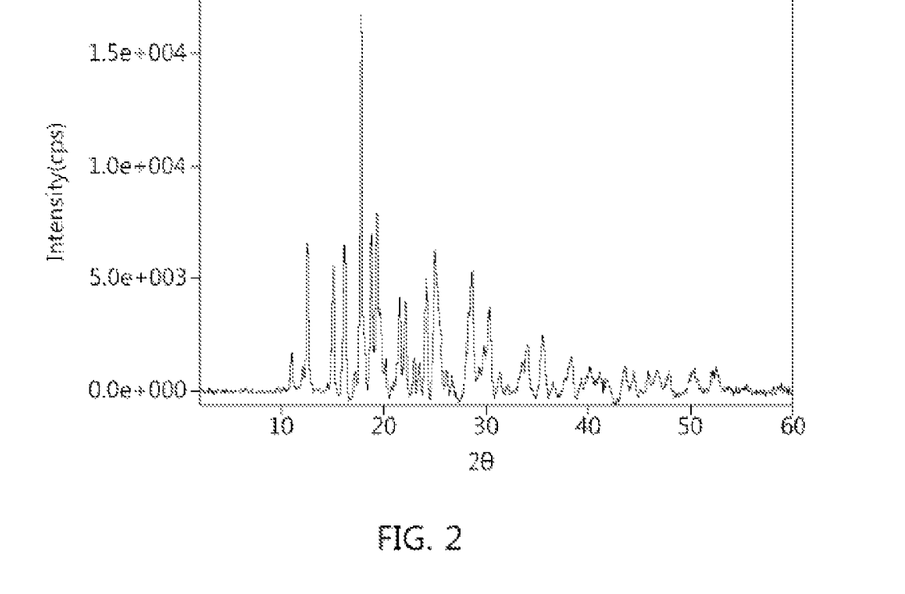
FIG. 2 is a graph showing the results of XRD of a Type VI doripenem anhydride crystal of Example 3 according to the present invention.

The Type VI doripenem anhydride crystal is a novel crystal having main peaks at diffraction angles (2θ) of 11.00±0.2, 12.55±0.2, 15.05±0.2, 16.18±0.2, 17.81±0.2, 18.83±0.2, 19.35±0.2, 21.56±0.2, 25.02±0.2 and 30.35±0.2° in a powder XRD pattern, and has the XRD values of FIG. 2.

Figure 10:
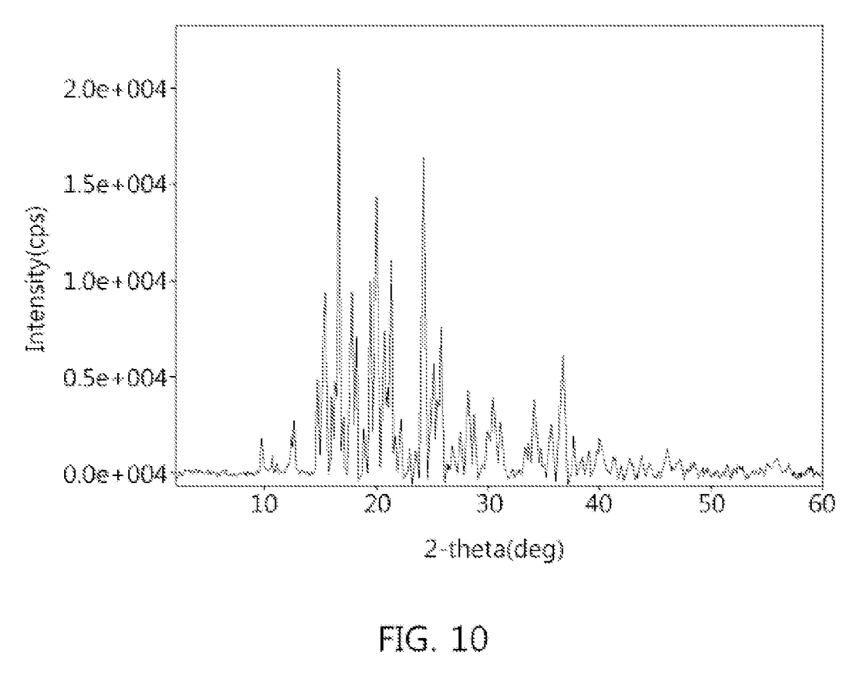
FIG. 10 is a graph showing the results of XRD of the Type VII doripenem anhydride crystal of Example 7 according to the present invention.

In addition, the Type VII doripenem anhydride crystal is a novel crystal has main peaks at diffraction angles (2θ) of 9.7±0.2, 12.7±0.2, 14.7±0.2, 15.4±0.2, 16.7±0.2, 17.8±0.2, 20.1±0.2, 21.3±0.2, 23.0±0.2, 24.3±0.2, 27.5±0.2, 30.5±0.2, 31.1±0.2 and 36.8±0.2° in a powder XRD pattern, and is characterized by the XRD values of FIG. 10.

Figure 5:
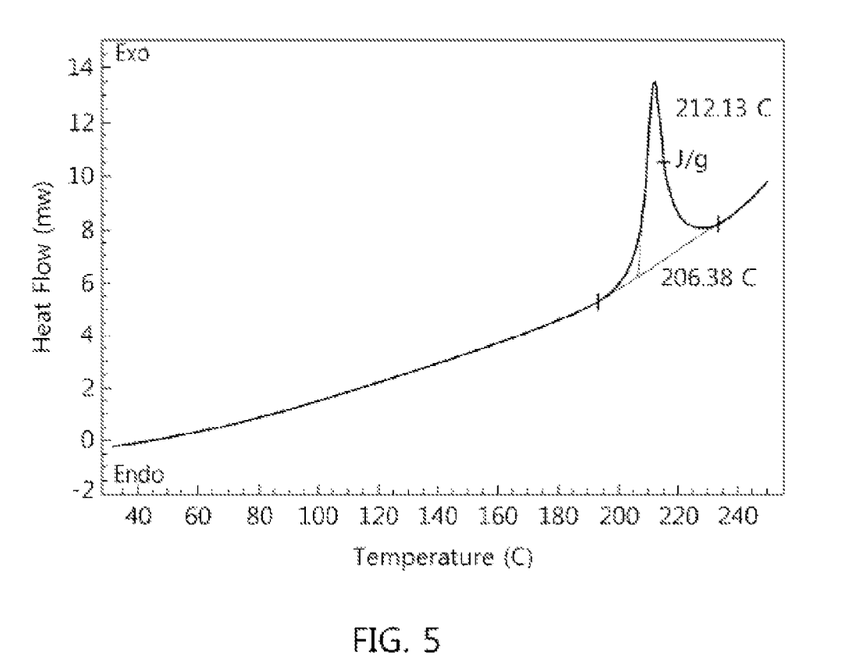
FIG. 5 is a graph showing the results of differential scanning calorimetry (DSC) of the Type VI doripenem anhydride crystal of Example 3 according to the present invention.

In addition, the Type VI doripenem anhydride crystal has a peak value at 200 to 220° C. in the DSC graph, and is characterized by the DSC values of FIG. 5.

Figure 11:
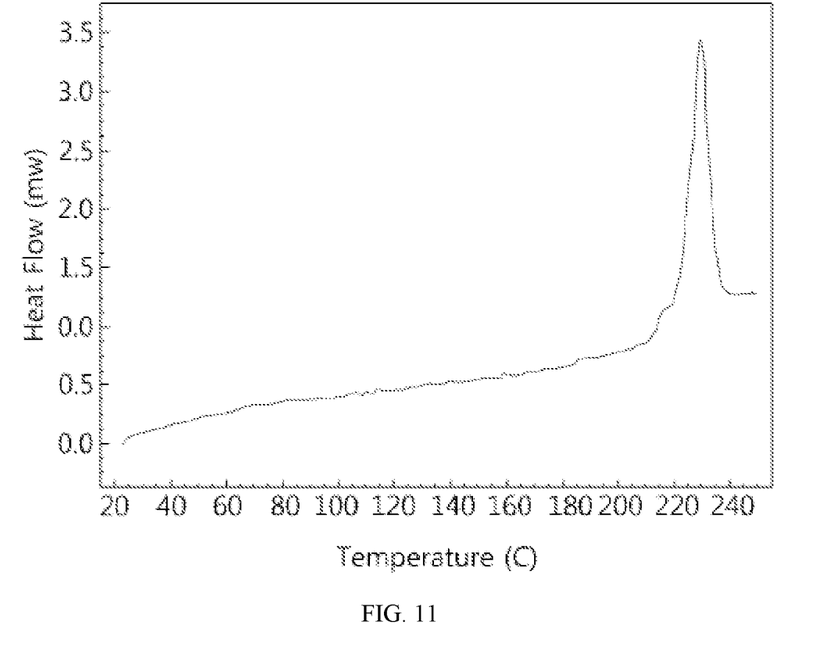
FIG. 11 is a graph showing the results of DSC of the Type VII doripenem anhydride crystal of Example 7 according to the present invention.

In addition, the Type VII doripenem anhydride crystal has a peak value at 200 to 220° C. in the DSC graph, and is characterized by the DSC values of FIG. 11.

In addition, the Type VI doripenem anhydride crystal has a water content of less than 2% and is characterized by a solubility of 55 to 65 mg/mL at 20 to 25° C.

In addition, the Type VII doripenem anhydride crystal has a water content of less than 2% and is characterized by a solubility of 30 to 35 mg/mL at 20 to 25° C.

The water content of the doripenem anhydride crystal is preferably in the range of 0.5 to 1%.

The present invention addresses a method of preparing the Type VI doripenem anhydride crystal and a method of preparing the Type VII doripenem anhydride crystal, which enable the preparation of the doripenem anhydride crystal at room temperature, facilitate the preparation thereof, and enable the preparation thereof in a short time due to the use of various solvents. The kind of solvent that is usable varies depending on the starting material of the doripenem anhydride crystal, and the preparation method according thereto is devised in the present invention.

Below is a description of the preparation of the Type VI doripenem using methods according to three embodiments of the present invention.

In the preparation method according to the first embodiment, doripenem used as the starting material is not particularly limited, but is preferably amorphous doripenem or a dimethyl sulfoxide solvate of doripenem, and the preparation method thereof includes the following steps:

(1) dissolving doripenem in ethylene glycol or dimethyl sulfoxide;

(2) adding a solution obtained in the step (1) to a mixture of methanol and water or a mixture of ethanol and water to produce a precipitate, the water being added in a volume of less than 15% but exceeding 0% based on the total volume of the methanol or ethanol in the mixture; and (3) filtering and drying the precipitate in the step (2), thus yielding a doripenem anhydride crystal.

In this method, doripenem used as the starting material is dissolved in ethylene glycol or dimethyl sulfoxide, and added with a mixed solution of methanol and water or a mixed solution of ethanol and water, thus forming a precipitate which is then aged, thereby yielding the doripenem anhydride crystal.

In addition, the water in (2) is used as a non-solvent, and functions to produce a crystal of the dissolved doripenem. The water has to be added in a volume of less than 15% but exceeding 0% based on the total volume of methanol or ethanol in a mixed solution. If the volume of water is 15% or more, the doripenem anhydride crystal is not produced, but Type III doripenem may result.

In the step (2), the produced precipitate is aged, and the aging time is in the range of 2 to 4 hr.

In the step (3), the aged precipitate is dried at 20 to 50° C., thus forming a doripenem anhydride crystal.

The preparation method according to the second embodiment uses Type III doripenem or Type IV doripenem as the starting material, and the prepation method thereof includes the following steps of:

(1) adding a Type III doripenem hydrate or a Type IV doripenem hydrate to any one selected from the group consisting of methanol, ethanol, a mixture of methanol and water, and a mixture of ethanol and water to produce a precipitate, the water being added in a volume of less than 15% but exceeding 0% based on the total volume of the mixture of methanol and water or the mixture of ethanol and water; and (2) filtering and drying the precipitate in the step (1), thus yielding a doripenem anhydride crystal.

When the Type III doripenem hydrate or the Type IV doripenem hydrate is used as the starting material, the solvent may include any one selected from the group consisting of methanol, ethanol, a mixture of methanol and water, and a mixture of ethanol and water. When the above mixture is used as the solvent, the water is added in a volume of less than 15% but exceeding 0% based on the total volume of the mixture. If the volume thereof is 15% or more, Type III or IV doripenem may be left behind.

In the step (1), the stirring time is set to 2 hr or longer. After the completion of the stirring process, in the step (2) is performed in a manner in which the precipitate is filtered, washed with an organic solvent, and dried at 20 to 50° C., thus obtaining a doripenem anhydride crystal.

The preparation method according to the third embodiment uses amorphous doripenem as the starting material, and includes the following steps of:

(1) adding amorphous doripenem to methanol or ethanol to produce a precipitate; and (2) filtering and drying the precipitate in the step (1), thus obtaining a doripenem anhydride crystal.

When amorphous doripenem is used as the starting material, methanol or ethanol may be used as the solvent.

In the step (1), the stirring time is set to 2 hr or longer. After the completion of the stirring process, in the step (2) is performed in a manner in which the precipitate is filtered, washed with an organic solvent, and dried at 20 to 50° C., thus obtaining a doripenem anhydride crystal.

In addition, the method of preparing Type VII doripenem is described below.

In this method, the form of doripenem that is used as the starting material is not particularly limited, but amorphous doripenem or a dimethyl sulfoxide solvate of doripenem may be preferably used, and the preparation method thereof includes the following steps of:

(1) dissolving doripenem in at least one solvent of N-methyl-2-pyrrolidone (NMP), dimethylformamide (DMF) and dimethylacetamide (DMAC);

(2) adding a solution obtained in the step (1) to a mixture of water and an organic solvent, thus producing a precipitate; and (3) filtering and drying the precipitate in the step (2), thus yielding a doripenem anhydride crystal.

In this method, doripenem used as the starting material is dissolved in at least one solvent of N-methyl-2-pyrrolidone (NMP), dimethylformamide (DMF) and dimethylacetamide (DMAC), and is added with a mixed solution of water and an organic solvent to give a precipitate, which is then aged, thereby yielding a doripenem anhydride crystal.

In addition, the water of step (2) is a non-solvent, and functions to produce a crystal of the dissolved doripenem.

In the step (2), the produced precipitate is aged, and the ageing time falls in the range of 2 to 4 hr.

In the step (3), the aged precipitate is dried at 20 to 50° C., resulting in a doripenem anhydride crystal.

All of the aforementioned four methods may be carried out at room temperature, and the prepared doripenem anhydride crystal (Type VI) has a solubility of 55 to 65 mg/mL at 20 to 25° C., and the prepared doripenem anhydride crystal (Type VII) has a solubility of 30 to 35 mg/mL at 20 to 25° C.

A conventional Type IV doripenem hydrate is used in a manner in which 10 mL of a saline is placed in a vial containing 0.25 g of Type IV doripenem to make a suspension, which is then completely dissolved in 100 mL of a saline using a syringe. The conventional Type IV doripenem hydrate has low solubility, and thus undissolved doripenem is left behind in the vial. Hence, when this doripenem is administered to patients, fixed-dose administration thereof is impossible.

However, the Type VI and Type VII doripenem anhydride crystals according to the present invention have high solubility and are completely dissolved in a solution without any remainder, and thus the above problem may be overcome.

In addition, the present invention addresses a solvate of doripenem, characterized in that the solvent used therefor is ethylene glycol or dimethyl sulfoxide.

The solvate of doripenem may be prepared in a manner in which doripenem is dissolved in ethylene glycol or dimethyl sulfoxide, added with a small amount of water, cooled, stirred, washed, and dried. The starting material for doripenem, which is used in the preparation of the solvate of doripenem, is not particularly limited.

Figure 1:
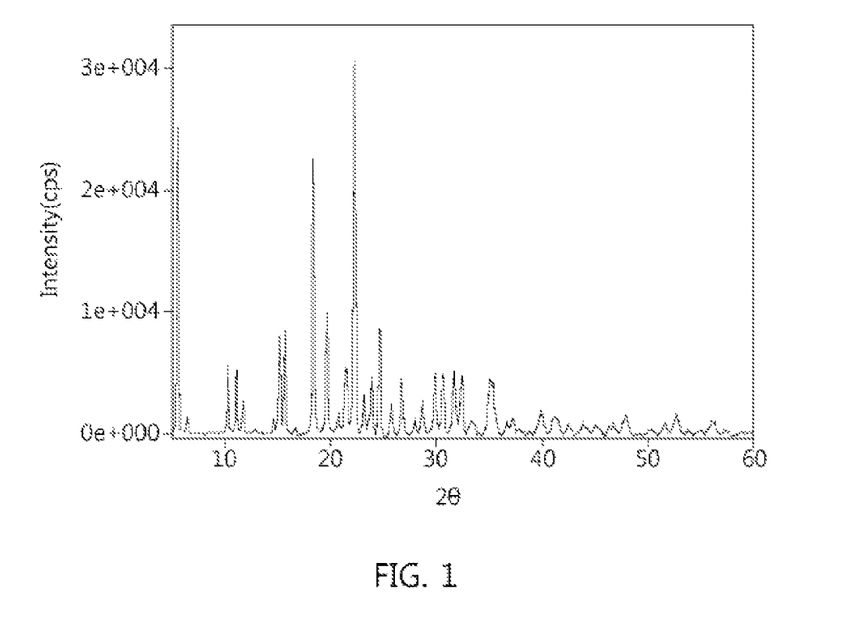
FIG. 1 is a graph showing the results of X-ray diffraction (XRD) of a dimethyl sulfoxide solvate of doripenem of Example 1 according to the present invention.

In addition, the dimethyl sulfoxide solvate of doripenem has main peaks at diffraction angles (2θ) of 5.5, 11.0, 11.7, 15.1, 15.6, 18.4, 21.4, 22.2, 23.8, 24.6, 29.8, 30.6, 31.6, 32.4, 35.0, and 35.3 in a powder XRD pattern (FIG. 1).

A better understanding of the present invention may be obtained via the following examples that are merely set forth to illustrate, and such examples may be appropriately modified and altered within the scope and spirit of the invention, as apparent to those skilled in the art, and attached claims obviously include such modified and altered examples.

<Preparation of Solvate of Doripenem>

Example 1

1 g of doripenem was dissolved in 5 mL of dimethyl sulfoxide. 4 mL of water was added at 20 to 25° C. After that, the resulting solution was then cooled to 0 to 5° C., stirred for 2 to 3 hr, filtered, washed with acetone, and dried at 20 to 25° C. for 15 hr, thus obtaining 850 mg of a dimethyl sulfoxide solvate of doripenem. The solvate was measured through XRD to observe the crystals, and the main peaks (2θ) were 5.5, 11.0, 11.7, 15.1, 15.6, 18.4, 21.4, 22.2, 23.8, 24.6, 29.8, 30.6, 31.6, 32.4, 35.0, and 35.3 (FIG. 1).

<Preparation Method 1. Preparation of Doripenem Anhydride Crystal>

Example 2

200 mg of amorphous doripenem was dissolved in 1 mL of dimethyl sulfoxide, added with 0.6 mL of water and 6 mL of ethanol, and stirred at room temperature for 3 hr to age a precipitate. The aged precipitate was filtered and dried at 40 to 45° C. for 15 hr, thus yielding 170 mg of a Type VI doripenem anhydride crystal.

Example 3

200 mg of amorphous doripenem was dissolved in 1 mL of dimethyl sulfoxide, added with 0.3 mL of water and 6 mL of ethanol, and stirred at room temperature for 3 hr to age a precipitate. The aged precipitate was filtered and dried at 40 to 45° C. for 15 hr, thus yielding 140 mg of a Type VI doripenem anhydride crystal.

Example 4

200 mg of amorphous doripenem was dissolved in 1 mL of dimethyl sulfoxide, added with 0.06 mL of water and 6 mL of ethanol, and stirred at room temperature for 3 hr to age a precipitate. The aged precipitate was filtered and dried at 40 to 45° C. for 15 hr, thus yielding 100 mg of a Type VI doripenem anhydride crystal.

Example 5

1 g of the solvate obtained in Example 1 was dissolved in 3 mL of NMP, added dropwise with an acetone aqueous solution (4.2 mL of H₂O and 12 mL of acetone), stirred for 1 hr, filtered, washed with acetone, and dried at 20 to 25° C. for 2 hr, thus yielding 698 mg of a Type VII doripenem anhydride.

Example 6

1 g of the solvate obtained in Example 1 was dissolved in 3 mL of DMF, added dropwise with an acetone aqueous solution (4.2 mL of H₂O and 12 mL of acetone), stirred for 1 hr, filtered, washed with acetone, and dried at 20 to 25° C. for 2 hr, thus yielding 690 mg of a Type VII doripenem anhydride.

Example 7

1 g of the solvate obtained in Example 1 was dissolved in 3 mL of DMAC, added dropwise with an acetone aqueous solution (4.2 mL of H₂O and 12 mL of acetone), stirred for 1 hr, filtered, washed with acetone, and dried at 20 to 25° C. for 2 hr, thus yielding 690 mg of a Type VII doripenem anhydride.

Comparative Example 1

200 mg of amorphous doripenem was dissolved in 1 mL of dimethyl sulfoxide, added with 1.2 mL of water and 6 mL of ethanol, and stirred at room temperature for 3 hr to age a precipitate. The aged precipitate was filtered and dried at 40 to 45° C. for 15 hr, thus yielding 140 mg of Type III doripenem.

Comparative Example 2

200 mg of amorphous doripenem was dissolved in 1 mL of dimethyl sulfoxide, added with 0.9 mL of water and 6 mL of ethanol, and stirred at room temperature for 3 hr to age a precipitate. The aged precipitate was filtered and dried at 40 to 45° C. for 15 hr, thus yielding 120 mg of Type IV doripenem.

<Preparation Method 2. Preparation of Doripenem Anhydride Crystal Using Type IV Doripenem Hydrate>

Example 8

1 g of Type IV doripenem was added to 28.5 mL of methanol and 1.5 mL of water and stirred at room temperature for 3 hr to produce a precipitate, which was then filtered and washed with acetone. The precipitate was dried at 40 to 45° C. for 15 hr, thus yielding 833 mg of a Type VI doripenem anhydride crystal.

Example 9

1 g of Type IV doripenem was added to 27 mL of methanol and 1.5 mL of water and stirred at room temperature for 3 hr to produce a precipitate, which was then filtered and washed with acetone. The precipitate was dried at 40 to 45° C. for 15 hr, thus yielding 843 mg of a Type VI doripenem anhydride crystal.

Example 10

1 g of Type IV doripenem was added to 30 mL of methanol and stirred at room temperature for 2 hr to produce a precipitate, which was then filtered and washed with acetone. The precipitate was dried at 30 to 35° C. for 15 hr, thus yielding 875 mg of a Type VI doripenem anhydride crystal.

Comparative Example 3

1 g of Type IV doripenem was added to 25.5 mL of methanol and 4.5 mL of water and stirred at room temperature for 3 hr to produce a precipitate, which was then filtered and washed with acetone. The precipitate was dried at 40 to 45° C. for 15 hr, thus yielding 850 mg of Type IV doripenem.

<Preparation method 3. Preparation of Doripenem Anhydride Crystal Using Amorphous Doripenem>

Example 11

1 g of amorphous doripenem was added to 30 mL of methanol and stirred at room temperature for 2 hr to produce a precipitate, which was then filtered and washed with acetone. The precipitate was dried at 30 to 35° C. for 15 hr, thus yielding 847 mg of a Type VI doripenem anhydride crystal.

Example 12

1 g of amorphous doripenem was added to 30 mL of ethanol and stirred at room temperature for 2 hr to produce a precipitate, which was then filtered and washed with acetone. The precipitate was dried at 30 to 35° C. for 15 hr, thus yielding 850 mg of a Type VI doripenem anhydride crystal.

Example 13

Among 50 g of amorphous doripenem, 5 g thereof was dissolved in 25 mL of dimethyl sulfoxide (DMSO), added dropwise to 1 L of 96% ethanol, and stirred for 3 hr. The remaining 45 g was dissolved in 225 mL of dimethyl sulfoxide (DMSO), further added dropwise to the ethanol, stirred for 1 hr, filtered, washed with acetone, and dried at 40 to 45° C. for 3 hr, thus yielding 40 g of a Type VI doripenem anhydride crystal.

Comparative Example 4

0.3 g of amorphous doripenem was added to 6 mL of isopropyl alcohol and stirred at room temperature for 3 hr to produce a precipitate, which was then filtered and washed with acetone. The precipitate was dried at 40 to 45° C. for 15 hr, thus yielding 223 mg of amorphous doripenem.

Comparative Example 5

0.3 g of amorphous doripenem was added to 6 mL of propanol and stirred at room temperature for 3 hr to produce a precipitate, which was then filtered and washed with acetone. The precipitate was dried at 40 to 45° C. for 15 hr, thus yielding 274 mg of amorphous doripenem.

Comparative Example 6. Type I Doripenem

Type I doripenem, as disclosed in PCT Publication Patent No. WO1995-029913, was used.

Comparative Example 7. Type II Doripenem

Type II doripenem, as disclosed in PCT Publication Patent No. WO1995-029913, was used.

Comparative Example 8. Type III Doripenem

Type III doripenem, as disclosed in PCT Publication Patent No. WO2001-072750, was used.

Comparative Example 9. Type IV Doripenem

Type IV doripenem, as disclosed in PCT Publication Patent No. WO2001-072750, was used.

Comparative Example 10. Type V Doripenem

Type V doripenem, as disclosed in PCT Publication Patent No. WO2008-006298, was used.

Test Example 1. Analysis of Doripenem Anhydride Crystal 1-1. XRD

Figure 4:
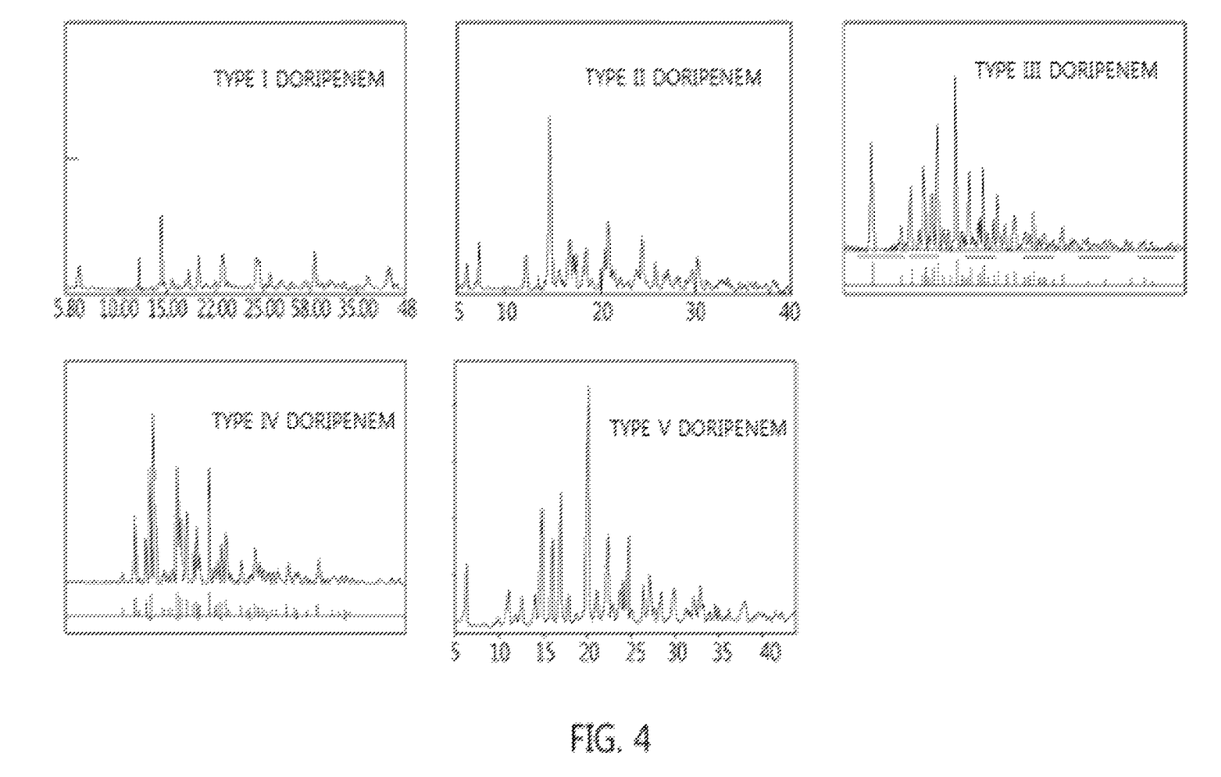
FIG. 4 is of graphs showing the results of XRD of Type 1 doripenem to Type V doripenem of Comparative Examples 6 to 10.

In order to analyze the solvate and the Type VI and VII doripenem anhydride crystals according to the present invention, XRD was performed. Table 1 below shows the anhydride crystal peaks of the solvate of Example 1 (FIG. 1), the Type VI doripenem anhydride crystal peaks of Example 3 (FIG. 2), the Type VII doripenem anhydride crystal peaks of Example 7 (FIG. 10) and peaks of Type I to V doripenem hydrates of Comparative Examples 6 to 10 (FIG. 4).

TABLE 1

| Crystal form | 2θ |
| --- | --- |
| C. Ex. 6 (Type I) | 7.32, 14.72, 18.62, 20.42, 21.1, 22.18, 23.88, 29.76 |
| C. Ex. 7 (Type II) | 6.06, 12.2, 14.56, 17.0, 18.38, 20.68, 24.38, 24.60, 25.88, 30.12 |
| C. Ex. 8 (Type III) | 6.78, 6.96, 15.74, 17.92, 21.16, 23.56, 25.80 |

TABLE 1-continued

| Crystal form | 2θ |
| --- | --- |
| C. Ex. 9 (Type IV) | 10.95, 13.12, 15.03, 15.95, 16.64, 18.14, 18.99, 19.71, 20.66, 21.12, 22.22, 23.40, 23.96, 26.13, 27.05, 27.51, 28.29, 29.02, 31.73, 33.45 |
| C. Ex. 10 (Type V) | 6.46, 15.27, 16.41, 17.49, 20.72, 23.05, 25.38 |
| Ex. 3 (Type VI) | 11.00, 12.55, 15.05, 16.18, 17.81, 18.83, 19.35, 21.56, 25.02, 30.35 |
| Ex. 7 (Type VII) | 9.7, 12.7, 14.7, 15.4, 16.7, 17.8, 20.1, 21.3, 23.0, 24.3, 27.5, 30.5, 31.1, 36.8 |

Figure 3:
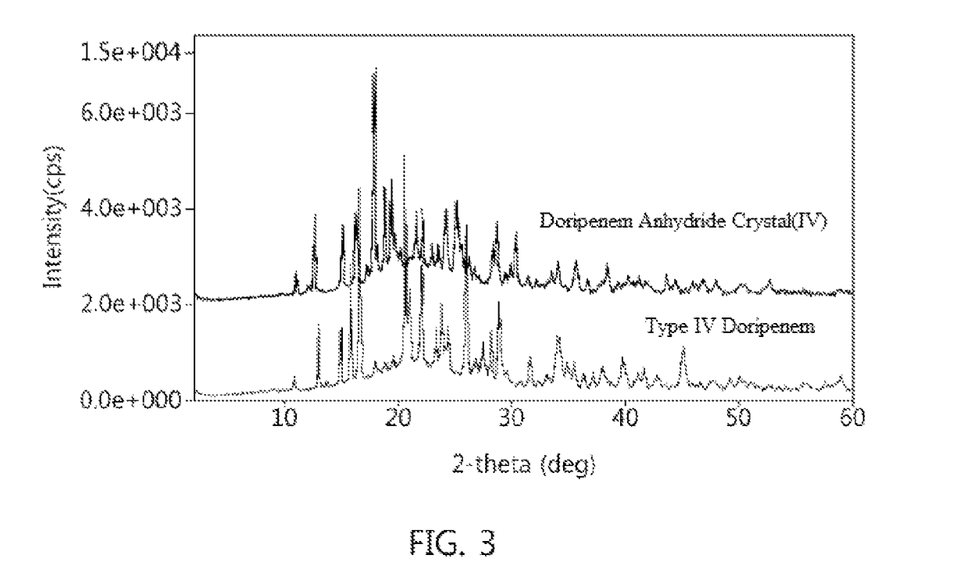
FIG. 3 is a graph showing the results of XRD of a Type VI doripenem anhydride crystal of Example 3 according to the present invention and Type IV doripenem of Comparative Example 9.

When comparing the results of XRD graph of the Type IV doripenem of Comparative Example 9 and the Type VI doripenem anhydride crystal of Example 3, the 2θ and intensity of the Type VI doripenem anhydride crystal of Example 3 were, when measured, found to be significantly different from those of the Type IV doripenem of Comparative Example 9, from which a novel doripenem crystal can be confirmed to result (FIG. 3).

In addition, based on the results of XRD of the doripenem anhydride crystal (Type VII) of Example 7, the 2θ and intensity of the doripenem anhydride crystal (Type VII) of Example 7 were, when measured, found to be significantly different from those of the Type IV doripenem of Comparative Example 9, from which a novel doripenem crystal can be confirmed to result.

1-2. DSC

Figure 6:
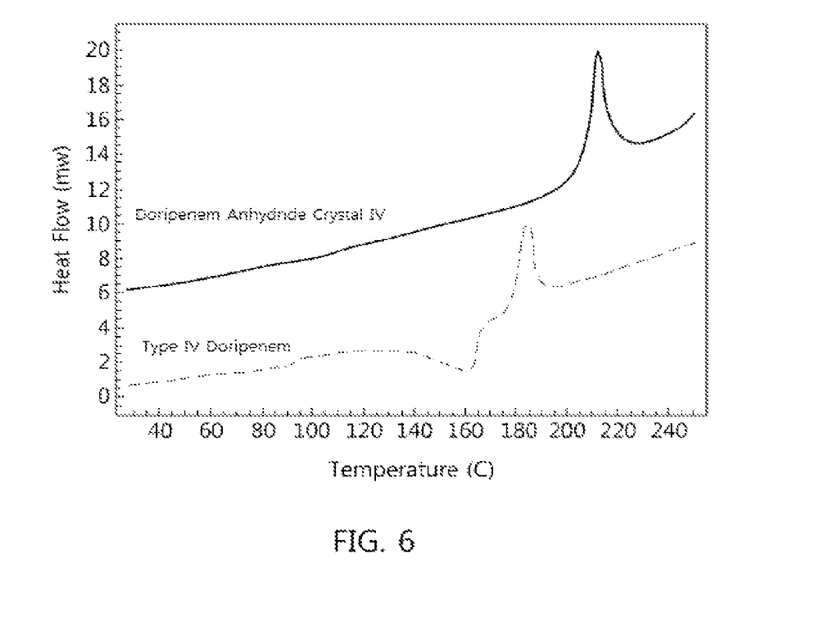
FIG. 6 is a graph showing the results of DSC of the Type VI doripenem anhydride crystal of Example 3 according to the present invention and the Type IV doripenem of Comparative Example 9.

When the Type VI doripenem anhydride crystal of Example 3 according to the present invention and the conventional Type IV doripenem were analyzed through differential scanning calorimetry (DSC), the decomposition temperature of the Type VI doripenem anhydride crystal was higher than that of the Type IV doripenem (FIG. 6). Thus, the Type VI doripenem anhydride crystal according to the present invention exhibited superior stability at high temperature, compared to the Type IV doripenem hydrate.

In addition, the decomposition temperature of the Type VII doripenem anhydride crystal of Example 7 according to the present invention was higher than that of the Type IV doripenem hydrate (FIG. 11). Thus, the Type VII doripenem anhydride crystal according to the present invention exhibited superior stability at high temperature compared to Type IV doripenem hydrate.

1-3. Measurement of Water Content

The doripenem anhydride crystals of Examples 3 and 7 according to the present invention and the Type IV doripenem hydrate of Comparative Example 9 were measured for water content. The results are shown in Table 2 below.

TABLE 2

| Crystal form | Water content |
| --- | --- |
| Example 3 (Type VI) | 0 to 2% |
| Example 7 (Type VII) | 0 to 2% |
| Comp. Example 9 (Type IV) | 4 to 5% |

Figure 7:
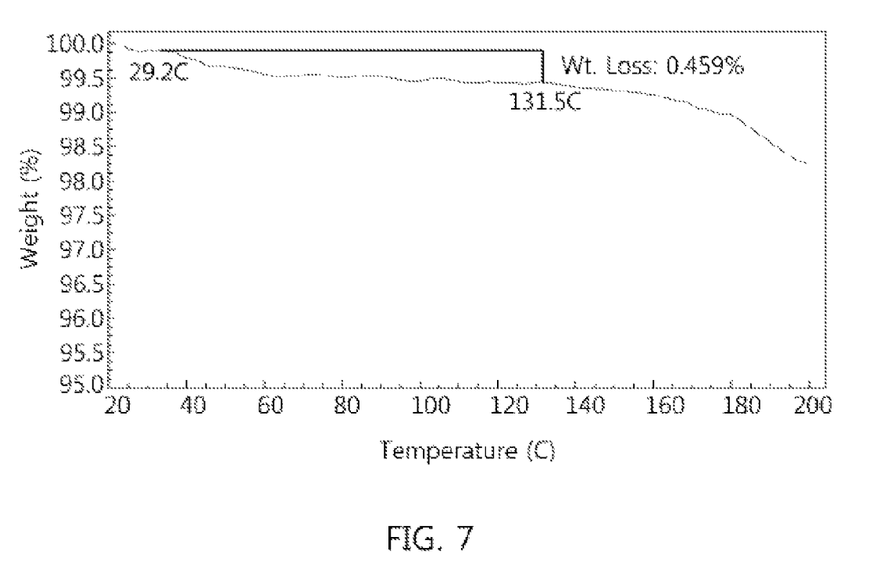
FIG. 7 is a graph showing the results of thermogravimetric analysis (TGA) of the Type VI doripenem anhydride crystal of Example 3 according to the present invention.
Figure 8:
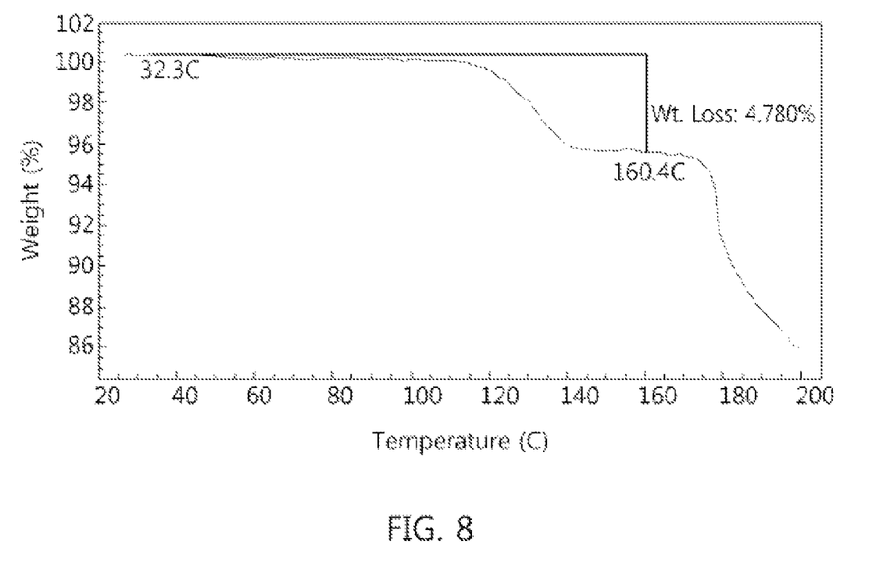
FIG. 8 is a graph showing the results of TGA of the Type IV doripenem of Comparative Example 9.
Figure 9:
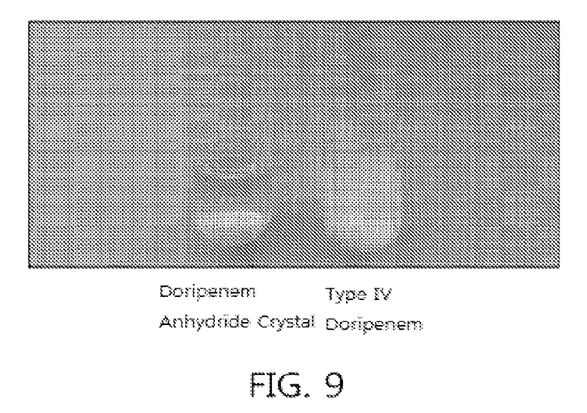
FIG. 9 is a photograph showing the solubility of the Type VI doripenem anhydride crystal of Example 3 according to the present invention and the Type IV doripenem of Comparative Example 9.

Based on the results of TGA, about 4.8% loss occurred in the Type IV doripenem of Comparative Example 9 (FIG. 8) and about 0.46% loss occurred in the Type VI doripenem anhydride crystal of Example 3 according to the present invention (FIG. 7). This means that the novel doripenem crystal, prepared through the method of the present invention, is an anhydride. Furthermore, the water content of the doripenem anhydride crystal according to the present invention was measured and found to be less than about 2%.

Test Example 2. Measurement of Solubility and Stability of Doripenem Anhydride Crystal The solubility of the Type VI doripenem anhydride crystal of Example 3 according to the present invention was measured and compared with that of the Type IV doripenem of Comparative Example 9.

50 mg of each of the Type VI doripenem anhydride crystal of Example 3 and the Type IV doripenem of Comparative Example 9 was added with water until the doripenem was completely dissolved, and the solubility thereof was measured. Meanwhile, 10 mL of water was added with the Type VI doripenem anhydride crystal of Example 3 and the Type IV doripenem of Comparative Example 9 until the doripenem was completely dissolved, and the solubility thereof was measured. As results, the solubility of the Type VI doripenem anhydride crystal of Example 3 was measured and found to be 55 to 65 mg/mL at 22° C. and the solubility of the Type IV doripenem of Comparative Example 9 was measured and found to be 20 mg/mL at 22° C.

Therefore, the Type VI doripenem anhydride crystal according to the present invention was confirmed to have remarkably high solubility compared to the conventional Type IV doripenem.

In addition, the Type VI doripenem anhydride crystal according to the present invention and the Type IV doripenem were allowed to stand at 60° C. for 3 weeks, and the purity thereof was measured to evaluate the stability. The results are shown in Table 3 below.

TABLE 3

| Duration | Example 3 (Doripenem anhydride crystal) Purity (%) | Comp. Example 9 (Type IV doripenem) Purity (%) |
|---|---|---|
| Initial | 99.6 | 99.8 |
| 1 week | 99.4 | 99.0 |
| 2 weeks | 98.8 | 98.2 |
| 3 weeks | 98.7 | 97.3 |

The purity of Example 3 (Type VI doripenem anhydride crystal) of the present invention was only decreased by less than 1% over time, but the purity of the Type IV doripenem was decreased by 2.56%.

Through the above testing, the Type VI doripenem anhydride according to the present invention was found to exhibit high stability compared to the conventional doripenem.

The solubility of the Type VII doripenem anhydride crystal of Example 7 was measured in the same manner as above, and was determined to be 30 to 35 mg/mL.

In addition, the Type VII doripenem anhydride crystal of Example 7 according to the present invention and the Type IV doripenem of Comparative Example 9 were allowed to stand at 60±5° C. for 3 weeks, and the purity thereof was measured to evaluate the stability. The results are shown in Table 4 below.

TABLE 4

| Duration | Example 7 (Type VII anhydride) Max. Amount of impurities (%) | Comp. Example 9 (Type IV hydrate) Max. Amount of impurities (%) |
|---|---|---|
| Initial | 0.06 | 0.06 |
| 1 week | 0.08 | 0.08 |
| 2 weeks | 0.08 | 0.23 |
| 3 weeks | 0.08 | 0.28 |

Over time, the maximum amount of impurities was increased by only 0.02% in the Type VII doripenem anhydride crystal of Example 7 of the present invention, but was increased by 0.22% in the Type IV doripenem of Comparative Example 9.

Through the above testing, the Type VII doripenem anhydride according to the present invention was found to exhibit high stability compared to conventional doripenem.

As is apparent from the above Test Examples, the novel doripenem crystal according to the present invention was confirmed to be in anhydride form and was found to exhibit superior solubility and stability.

The invention claimed is:

1. A doripenem crystal characterized by peak values of 11.00±0.2, 12.55±0.2, 15.05±0.2, 16.18±0.2, 17.81±0.2, 18.83±0.2, 19.35±0.2, 21.56±0.2, 25.02±0.2, and 30.35±0.2° in an X-ray diffraction (XRD) graph.

2. The doripenem crystal of claim 1, characterized by an XRD value of FIG. 2.

3. A doripenem crystal characterized by peak values of 9.7±0.2, 12.7±0.2, 14.7±0.2, 15.4±0.2, 16.7±0.2, 17.8±0.2, 20.1±0.2, 21.3±0.2, 23.0±0.2, 24.3±0.2, 27.5±0.2, 30.5±0.2, 31.1±0.2, and 36.8±0.2° in an XRD graph.

4. The doripenem crystal of claim 3, characterized by an XRD value of FIG. 10.

5. The doripenem crystal of claim 1, characterized by a peak value at 200 to 240° C. in a differential scanning calorimetry (DSC) graph.

6. The doripenem crystal of claim 5, characterized by a DSC value of FIG. 5.

7. The doripenem crystal of claim 3, characterized by a peak value at 200° to 240° C. in a differential scanning calorimetry graph.

8. The doripenem crystal of claim 1, characterized in that the doripenem crystal has a water content of less than 2%.

9. The doripenem crystal of claim 1, characterized in that the doripenem crystal has a solubility of 55 to 65 mg/mL at 20 to 25° C.

10. A method of preparing a doripenem crystal, comprising:
(1) dissolving doripenem in ethylene glycol or dimethyl sulfoxide;
(2) adding a solution obtained in the step (1) to a mixture of methanol and water or a mixture of ethanol and water to produce a precipitate, the water being added in a volume of less than 15% but exceeding 0% based on a total volume of methanol or ethanol in the mixture; and
(3) filtering and drying the precipitate in the step (2).

11. An ethylene glycol or dimethyl sulfoxide solvate of doripenem.

12. The doripenem crystal of claim 7, characterized by DSC value of FIG. 11.

13. The doripenem crystal of claim 3, characterized in that the doripenem crystal has a water content of less than 2%.

14. The doripenem crystal of claim 3, characterized in that the doripenem crystal has a solubility of 30 to 35 mg/mL at 20 to 25° C.

* * * * *